United States Patent [19]
Feldman et al.

[11] Patent Number: 6,029,526
[45] Date of Patent: Feb. 29, 2000

[54] METHOD AND APPARATUS FOR MEASURING IN SITU OR STRESS OF CONCRETE

[75] Inventors: Alex I. Feldman, Redmond, Wash.; Gerard J. Buechel, Brookline, Mass.; Hollie L. Ellis; Michael S. Kucker, both of Seattle, Wash.

[73] Assignee: Shannon & Wilson, Inc., Seattle, Wash.

[21] Appl. No.: 09/079,135

[22] Filed: May 14, 1998

[51] Int. Cl.⁷ .................................................. G01N 33/38
[52] U.S. Cl. .............................................. 73/803; 73/786
[58] Field of Search ........................... 73/786, 787, 789, 73/799, 803, 784, 774

[56] References Cited

U.S. PATENT DOCUMENTS

| | | | |
|---|---|---|---|
| 3,600,938 | 8/1971 | Waddell et al. | 73/88 E |
| 3,765,230 | 10/1973 | Bohm et al. | 73/88 R |
| 3,792,608 | 2/1974 | Holm et al. | 73/803 |
| 3,961,524 | 6/1976 | de la Cruz | 73/783 |
| 4,155,264 | 5/1979 | Bender et al. | 73/783 |
| 4,389,896 | 6/1983 | Babcock | 73/784 |
| 4,748,855 | 6/1988 | Barnoff | 73/803 |
| 4,860,587 | 8/1989 | Keller | 73/774 |
| 4,962,668 | 10/1990 | Preston et al. | 73/784 |
| 5,377,548 | 1/1995 | Ballivy | 73/768 |
| 5,487,307 | 1/1996 | Landgren et al. | 73/803 |
| 5,520,055 | 5/1996 | Füssinger | 73/762 |
| 5,576,494 | 11/1996 | Osterberg | 73/784 |
| 5,608,169 | 3/1997 | Fujioka et al. | 73/803 |

FOREIGN PATENT DOCUMENTS

| | | | |
|---|---|---|---|
| 597944 | 2/1978 | U.S.S.R. | G01N 3/08 |

*Primary Examiner*—Max Noori
*Attorney, Agent, or Firm*—Seed Intellectual Property Law Group PLLC

[57] ABSTRACT

Method and apparatus for measuring in situ the strain and stress of concrete, and having an initial stress resulting from existing stress in the concrete and stress caused from varying externally applied forces on the concrete, by placing a strain gauge on an outer face of the concrete and reading the output to determine an original baseline reading, then cutting spaced slots above and below the gauge to define a segment of the concrete, placing flat jacks into the slots, pressurizing the flat jacks to restore the initial strain to the original baseline reading in the gauge to determine the initial stress in the segment, as alternatives, then leaving the flat jacks pressurized with constant pressure in the slots to measure variations in the strain in the segment over a period of time caused by creep in the concrete, or determining the modulus of elasticity of the concrete by incrementally varying the pressure on the segments while measuring corresponding strain, or adding an adjacent strain gauge to measure the stress caused by a change in the applied external load.

19 Claims, 2 Drawing Sheets

METHOD AND APPARATUS FOR MEASURING IN SITU OR STRESS OF CONCRETE

TECHNICAL FIELD

This invention relates to measuring in situ stress or strain of concrete.

BACKGROUND OF THE INVENTION

It is often necessary to measure the existing stress or strain in concrete structures at any point in time and to determine the changes in the stress either from externally applied varying loads on the concrete, changes in temperature or moisture, or long term creep [creep is defined as the deformation in concrete occurring under, and induced by, a constant sustained stress]. For example, the concrete liner of a tunnel can have a static load from the weight of the soil and varying loads from the addition or excavations of the soil above the tunnel. Measuring concrete in situ stress or strain is not easily done because concrete has a non-uniform structure composed of aggregate of varying size and a binder material. Furthermore, concrete is a relatively stiff material which makes accurate measurements of strain difficult.

Various techniques have been employed to measure in situ stress or strain in materials. One technique includes attaching a strain gauge on mounting blocks on an in situ volume of the material to establish a baseline reading, then removing the strain gauge and making a slot in between the mounting blocks of the strain gauge on the volume of material, then replacing the strain gauge, applying pressure on the walls of the slot using a flat jack, and measuring the change in strain to establish the strain that existed in the volume of material before the slot was cut. The pressure applied in the flat jack that restores the baseline reading of the train gauge corresponds to the in situ stress.

This technique has not generally been applied to concrete. As mentioned above, concrete is a relatively stiff material and thus the amount of deformation of the material before and after the slot is cut is very small and measuring the change in strain is very difficult. A major drawback of this technique is that the removal of the gauge to cut the slot will create errors in the readings even if the gauge is attempted to be placed back in the same position. Furthermore, determining an in situ modulus of elasticity of the material with this technique is not practicable.

A second technique is to attach a strain gauge in situ on a volume of concrete, then cut a circular slot around the strain gauge to define a concrete segment. However, with this technique the gauge is not readable while cutting and the circular slot is not suitable for subsequently re-applying pressure on the segment with jacks.

In these techniques in situ stress must be determined from the measured change in strain and from a modulus of elasticity determined by laboratory methods.

Accordingly a need has arisen for measuring in situ stress or strain with more accuracy in concrete structures, as well as in situ measurements of modulus of elasticity, long term creep, or direct measurements of in situ stress caused by a change of external load.

SUMMARY OF THE INVENTION

An object of the invention is to make more accurate measurements of in situ strain or stress of concrete.

Another object of the invention is to directly measure in situ stress change in concrete caused by a change of external load on the concrete.

Another object of the invention is to measure in situ strain caused by creep in concrete.

Another object of the invention is to determine in situ the modulus of elasticity of concrete.

Basically, one aspect of the method of the invention is to firmly attach a strain gauge on the outer face of a volume of the concrete to establish a baseline reading, then cut slots above and below the gauge to define a free segment in the concrete, place flat jacks (thin flat walled containers filled with fluid and connected to a pressuring source with the walls of the jacks being flexible to transfer the pressure from the jacks to the walls of the slots) into the slots, pressurize the flat jacks to restore the gauge to its original baseline strain reading, and then to determine directly from measuring the pressure in the flat jacks the initial in situ stress in the segment that existed prior to cutting the slots. This stress measurement is important to determine the stress existing in the concrete built up perhaps over a long period of time.

Additionally, measurements of strain caused by creep in the segment can be made continuously over a period of time by maintaining the pressure in the jacks at a constant pressure and measuring any change in strain during the period.

Further, if a measurement of the modulus of elasticity of the segment is desired, this also can be accomplished by varying the pressure in the flat jacks in predetermined amounts and reading the corresponding changes in output reading in the strain gauge.

Still further, a direct measurement of the change in stress in the concrete can be made by placing a second strain gauge adjacent to the segment but far enough away as to not be influenced by the slots, with the adjacent strain gauge having the same output as the strain gauge on the segment when no pressure is being applied by the flat jacks, applying an external load on the concrete to produce a change in the output of the adjacent strain gauge, then applying pressure to the flat jacks to produce the same change in the output of the strain gauge on the segment and reading directly the pressure in the flat jacks that will correspond to the stress in the concrete caused by the externally applied load.

Preferably the apparatus of the invention includes a strain gauge attached to the outer face of a segment of concrete, the segment being defined by a pair of spaced slots to form spaced side walls in the slots; a flat jack in each slot, the flat jacks having expandable surfaces that push against the inner side walls of the slots, a fluid pressure source connected to the flat jacks to apply pressure to the flat jacks which in turn apply pressure to side walls of the slots; whereby the flat jacks can restore the stress initially in the segment and this stress can be read directly from the pressure in the flat jacks. The pressurizing source to the jacks includes a constant pressure source, such as an adjustable spring or a constant air pressure, to be used during the measurement of in situ strain in the concrete. A pressure gauge is connected to the flat jacks fluid pressure source to measure the pressure applied to the segment directly.

Another apparatus includes an adjacent strain gauge having an output that will change due to a change in the external applied load to the concrete. This adjacent strain gauge in combination with the strain gauge attached to the outer face of the segment of concrete, with the flat jacks applying the pressure necessary to bring the strain gauge on the segment back to the same output as that of the adjacent strain gauge after the load was applied will allow a measurement directly of the change in stress of the concrete caused by the applied load by directly reading the pressure in the flat jacks necessary to bring the change in strain in the segment gauge equal to the change in strain in the adjacent gauge caused by the externally applied load.

DETAILED DESCRIPTION OF THE INVENTION

As shown in the drawings a typical structure, such as, the concrete liner around an underground tunnel, and for purposes of the description, a tunnel also lying beneath the floor of an ocean bay subjected to the varying weight of dredging or soil filling loads, is shown as having a volume C taken at one or more locations in the concrete. The concrete is of the type composed of an aggregate (rocks, pebbles, and sand of varying sizes and shapes) joined by a cement paste or binder as is well known in the art. The tunnel liner may be very old perhaps built in the early 1900's or can be newer concrete. It should be understood that the invention is useable with any concrete structure of any age and that the example of a tunnel liner is for purposes of illustration only.

Attached to the outer wall or accessible face 12 of the volume C is a conventional strain gauge 30 of the type used for attaching to the relatively rough surface of concrete. A typical strain gauge for this purpose is model 4000, manufactured by Geokon, Inc., located at Lebanon, N.H. The strain gauge typically will have an effective gauge length and a longer housing.

After the strain gauge 30 is attached firmly to the face of the volume of concrete as by epoxy adhesives or other suitable fasteners, the reading of the strain gauge is taken to form a baseline reading. Then a pair of slots 10 and 11 are cut into the concrete to define a free segment S. The strain can be measured as the slots are cut as the strain gauge remains active before, during, and after the slots are cut.

The slots 10 and 11 are cut using a rotary concrete saw and the strain measurements can continue as the slots are cut. In one example for a two foot thick concrete tunnel liner the slots are about eight inches apart, the strain gauge is about six inches in length, the slots about four inches deep and twelve inches long with rounded inner ends and cut with a typical powered round concrete cutting blade. Placed into the slots are flat jacks 14 and 16 whose side walls are flexible and can, when pressurized, expand to press uniformly against the side walls of the slots. The flat jacks are shaped to conform to the shape of the slots to fill the slots and are connected to a pressurizing source, that preferably can be maintained at a constant pressure as well as having a controlled variable pressure. A typical pressurizing source is shown at 20 and has hydraulic fluid lines connected to a fluid chamber that is pressurized by an adjustable spring or an air source as is well known. A pressure gauge G and a regulator R are connected to the hydraulic lines to measure and regulate the pressure being placed into the jacks.

In the method, the pressure in the jacks is increased until the strain gauge again reads the baseline readout [it being understood that when the slots are cut to define the walls of the segment S, the stress on the segment before cutting the slots is relieved and the segment will expand]. By applying the pressure through the flat jacks the original stress in the segment can be restored and this pressure measured directly by the gauge G. Since the strain gauge has not been removed, this restoration of the strain in the segment can be accurately measured by reading the output of the strain gauge.

Advantageously with this method and apparatus, the strain gauge and pressurized flat jacks may be left in place and further measurements of the strain of the concrete may be made. One example is to measure the strain caused by creep of the concrete under constant flat jack pressure load over a period of time. Assuming no unusual external loads are applied, any deformation of the concrete due to creep will now be measured by the strain gauge.

Figure 3:
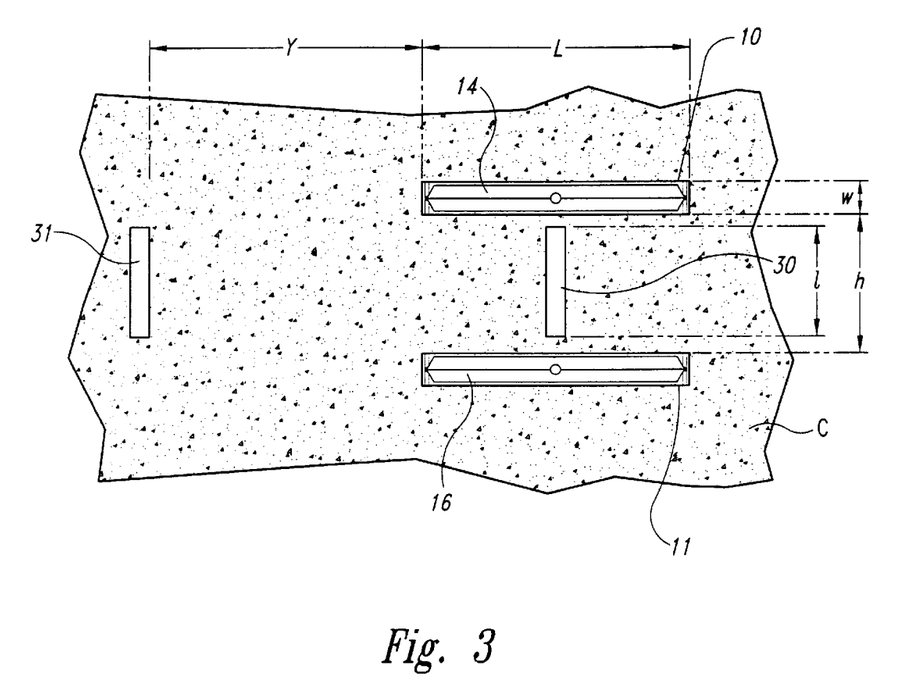
FIG. 3 is a partial front elevation of the concrete to be studied as viewed also in the same general direction of the arrows in FIG. 1 but of a modified embodiment of the invention using an adjacent second strain gauge.

A further application of the method is to apply an adjacent second strain gauge 31 close to the strain gauge on the segment but far enough away a distance Y, not less than one h, about eight inches for the example already given) as to not be influenced by the slots, it being understood that both strain gauges will be oriented the same direction and in the anticipated direction of the maximum compressive stress, then relieve the pressure in the flat jacks, set the output of the two strain gauges equal or start them with known readings, apply an external load to the concrete as, for example, adding soil above the concrete to cause a change in the output of the adjacent strain gauge, then increase the pressure in the flat jacks until the strain gauge on the segment shows the same change in reading as the output of the adjacent gauge, and read the stress caused by the external load directly by reading the pressure in the flat jacks. If the applied external load is negative, that is, an external load is removed from the concrete, the procedure is to first pressurize the flat jacks and set the adjacent strain gauge at the same reading as the strain gauge on the segment or start both strain gauges with known readings. Then by locking the pressure in the flat jacks constant and then removing the external load, the pressure in the flat jacks can then be reduced until the change in the reading of the strain gauge on the segment is the same as the change in the reading of the adjacent strain gauge. This change in pressure will directly show the stress caused by the removed external load.

Still further the method can be advantageously employed to measure the modulus of elasticity of the concrete in the segment by incrementally increasing the pressure in the jacks and measuring the resulting strain in the segment using the strain gauge.

Figure 2:
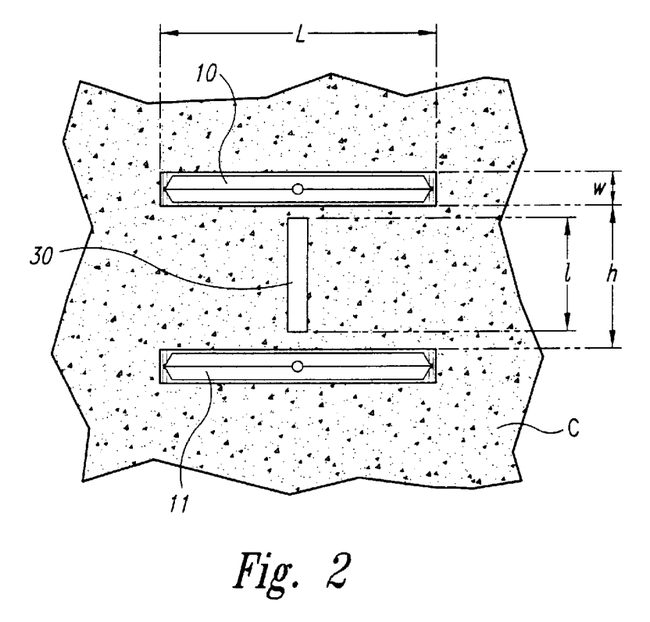
FIG. 2 is a partial front elevation of the concrete to be studied as viewed in the direction of the arrows in FIG. 1.

Preferably the depth d of the slots, the distance h between the slots [the height of the segment S], and the effective length I of the strain gauge perpendicular to the two slots are a function of the size of the largest aggregate in the segment. The gauge length I should be three to four times the diameter of the largest aggregate expected in the segment. The distance h between the slots should allow for about one-half inch space between the closest wall of the slots and the ends of the length of the strain gauge housing for allowing clearance for the saw blade. For one example, with two inch diameter maximum aggregate, the effective length of the strain gauge will be between six–eight inches. Assuming about six and one-half inch total overall length of the gauge [including the housing for the gauge] is used, the edges of the closest walls of each slot should be ½ inch from the ends of the strain gauge housing. This will make the height of the segment to be about seven and one-half inches (six and one-half inches+½ inch+½ inch=seven and one-half inches or about eight inches). To free the stress in the segment the depth of the slots should be not less than one-half the distance h between the slots. The depth d of the slots for the example given is at least four inches. The slot width w is of normal concrete saw blade thickness of about ¼ inch. The depth d of each slot should be not less than the one half of height h of the segment. The horizontal length of the slot L should be equal to or greater than two times h in order to free the segment sufficiently from the external load or make the stresses in the area of the gauge on the segment zero. The length L of the slot should thus be at least sixteen inches for the example given.

Figure 1:
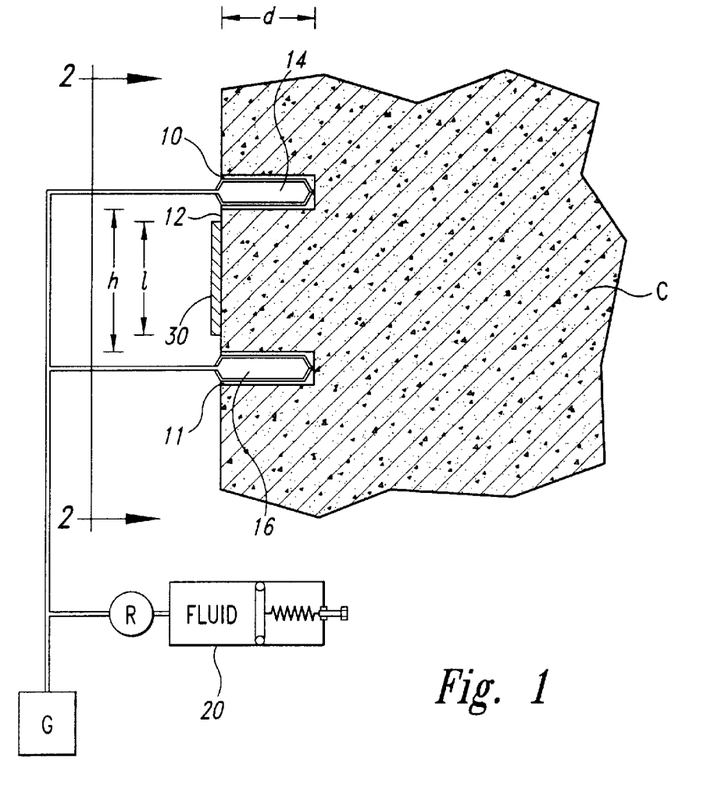
FIG. 1 is a schematic vertical section through a typical concrete structure such as the wall of a tunnel liner to be examined for its stress and strain.

The apparatus of the invention is best explained again from FIG. 1, the strain gauge 30 is attached to the face 12 of the segment, the slots 10 and 11 are cut, the flat jacks 14 and 16 are the placed in the slots and the pressure source 20 connected. The flat jacks are two flat copper plates soldered together at their edges and, of course, are relatively thin to fit into the slots. Preferably again the pressure source includes both a constant and variable pressure supply and the gauge G is applied to measure the applied hydraulic pressure. With this apparatus, measurements can be made of changes in strain caused by varying the pressure applied by the flat jacks, the stress in the segment can be measured directly from the pressure gauge connected to the flat jacks, and strain measurements caused by creep can be made by maintaining the pressure constant in the flat jacks and measuring changes in strain over a period of time. As is readily apparent, the pressure in the flat jacks must be the same pressure in each flat jack for making measurements.

The apparatus may include an adjacent strain gauge 31 for measuring in combination with the gauge 30, and flat jacks 14 and 16, the change in stress caused by a change in external load.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. The method of measuring in situ strain and stress on the surface of the concrete of concrete structures, comprising:

attaching directly to the surface of the concrete in its original state at a desired segment a strain measuring device and determining a baseline reading from the strain measuring device;

cutting a slot on two opposed sides of the segment with the strain measuring device still attached and measuring a new reading on the strain measuring device showing the relaxed state of the segment; and placing a flat jack in each slot and pressurizing the flat jacks at the same pressure until the strain returns to the baseline reading of the strain measuring device which shows the change in the strain of the segment with the pressure placed into the flat jacks equaling the stress in the segment prior to cutting the slots and thus the initial existing stress in the concrete of the segment.

2. The method of claim 1, wherein the pressure in the jacks is maintained at a constant pressure for a period of time while the segment is under constant or no unusual external load to measure creep.

3. The method of claim 1, adding an adjacent strain gauge adjacent to the strain gauge on the segment, applying an external load to the concrete to produce a change in the output reading of the adjacent strain gauge, then changing the pressure in the flat jacks to produce the same change in output reading on the segment strain gauge as will appear on the adjacent strain gauge to directly measure the stress caused by the externally applied load by directly reading the change in pressure in the flat jacks.

4. The method of claim 1, wherein the pressure in the jacks is incrementally varied and the strain measured by the gauge on the segment with each variation to determine the modulus of elasticity of the concrete.

5. The method of measuring in situ strain or stress on the surface of the concrete of a concrete structure, comprising:

attaching to the surface of the concrete at a desired segment a strain measuring device;

cutting a slot on two opposed sides of the segment with the strain measuring device still attached; and placing a flat jack in each slot and pressurizing the flat jacks with a pressure to measure the change in strain caused by any change in pressure.

6. The method of claim 5, wherein the pressure in the flat jacks is maintained constant and the change in strain measured is caused by creep.

7. The method of claim 5, wherein the pressure in the flat jacks is varied incrementally and the corresponding change in strain is measured to determine the modulus of elasticity in the segment.

8. The method of claim 5, wherein the pressure in the flat jacks is increased until the strain in the segment is equals the original output reading on the strain gauge when first applied to the segment before the slots were cut to determine the stress existing in the concrete before the slots were cut.

9. The method of claim 5, including adding an adjacent strain gauge adjacent to the strain gauge on the segment, applying an external load to the concrete to produce a change in the output reading of the adjacent strain gauge, then changing the pressure in the flat jacks to produce the same change in output reading on the segment strain gauge as will appear on the adjacent strain gauge to directly measure the stress caused by the externally applied load by directly reading the change in pressure in the flat jacks.

10. The method of claim 5, wherein the strain is measured while the slots are cut in the concrete.

11. Apparatus for measuring in situ strain and stress on the surface of the concrete of a concrete structure having a segment defined by a pair of spaced slots cut into the concrete, the segment having inner spaced wall surfaces and an outer end surface, the concrete in the segment having an initial stress caused by the existing stress in the concrete and the externally applied forces to the concrete before the slots are cut, comprising:

a strain gauge attached to the outer end surface of the segment;

a flat jack in each slot, the flat jacks having expandable flexible surfaces that push against the spaced inner wall surface of the slots; and a fluid pressure device connected to the flat jacks to apply pressure to the flat jacks which in turn apply pressure to the slot side walls, whereby the flat jacks can restore the initial existing stress into the segment, and then can also measure changes in the strain by subsequent changes in the external loads applied to the concrete or from creep in the concrete.

12. The apparatus of claim 11, said fluid pressure device including a constant pressure source for applying a constant pressure on the segment for a period of time with no unusual externally applied loads to measure the strain caused by creep in the concrete.

13. The method of measuring in situ strain and stress of concrete, comprising:

attaching to the concrete at a desired segment a strain measuring device and determining a baseline reading from the strain measuring device;

cutting a slot on two opposed sides of the segment with the strain measuring device still attached and measuring a new reading on the strain measuring device showing the relaxed state of the test segment;

placing a flat jack in each slot and pressurizing the flat jacks at the same pressure until the strain returns to the baseline reading of the strain measuring device which shows the change in the strain of the test segment with the pressure placed into the flat jacks equaling the pressure or stress in the test segment prior to cutting the slots and thus the initial existing stress in the concrete of the test segment; and said strain gauge having a length, the length of the strain gauge being aligned perpendicular to the spaced slots, the gauge length being about three to four times the diameter of the largest aggregate expected in the segment, the space between the slots being providing about one-half inch space between the closest wall of the slots and the ends of the length of the strain gauge, the slot depth being not less than one-half the distance between the slots, the length of the slot being two times the distance between slots.

14. The apparatus of claim 11, including an adjacent strain gauge, the combination of the two gauges, the slots, the flat jacks, pressure source and pressure gauge being able to measure directly the change in stress caused by a change in external applied load.

15. Apparatus for measuring in situ strain and stress in a concrete structure having a segment defined by a pair of spaced slots having spaced side walls cut into the concrete, the segment having inner spaced wall surfaces and an outer end surface, comprising:

a strain gauge attached to the outer end surface of the segment;

a flat jack in each slot, the flat jacks having expandable surfaces that push against the side walls of the slots; and a fluid pressure device connected to the flat jacks to apply a change in pressure to the flat jacks which in turn apply pressure to the slot side walls, to determine the changes in stress in the segment, the strain gauge attached to the segment detecting changes in the segment.

16. The apparatus of claim 15, including a constant pressure source to maintain a constant pressure in the fluid pressure device to measure the change in strain caused by creep in the concrete.

17. The apparatus of claim 15, including a variable pressure source to vary the pressure in the fluid pressure device to vary incrementally the pressure in the flat jacks and the corresponding strain is measured to determine the modulus of elasticity in the segment.

18. The apparatus of claim 15, including a variable pressure source to vary the pressure in the fluid pressure device to increase the pressure in the flat jacks until the strain in the segment is equal to the original output reading on the strain gauge when first applied to the segment before the slots were cut.

19. The apparatus of claim 15, including a second strain gauge attached to the surface of the segment adjacent to the first strain gauge to obtain an output reading when a change occurs on the external loading of the concrete structure, and wherein the pressure source and the fluid pressure device change the pressure in the flat jacks to produce the same change in the output reading on the first strain gauge to match the output reading of the adjacent second strain gauge to directly measure the stress caused by the externally applied load by directly reading the change in pressure in the flat jacks.

* * * * *

UNITED STATES PATENT AND TRADEMARK OFFICE
CERTIFICATE OF CORRECTION

PATENT NO. : 6,029,526
DATED : Feb. 29, 2000
INVENTOR(S) : Alex I. Feldman, et al.

It is certified that error appears in the above-identified patent and that said Letters Patent is hereby corrected as shown below:

The Title, "METHOD AND APPARATUS FOR MEASURING IN SITU AND STRESS OF CONCRETE" should read --METHOD AND APPARATUS FOR MEASURING IN SITU STRAIN AND STRESS OF CONCRETE--.

The first line of the abstract, "in situ the strain" should read --in situ strain--.

Column 1, line 6, "in situ stress or strain" should read --in situ strain or stress--.

Column 1, line 28, "slot in between" should read --slot between--.

Column 1, line 34, "train gauge" should read --strain gauge--.

Column 1, line 53, "In these techniques in situ" should read --In these techniques, in situ--.

Column 1, line 56, "Accordingly a need" should read --Accordingly, a need--.

Column 2, lines 3-4, "determine in situ the modulus" should read --determine the in situ modulus--.

Column 2, line 7, "the concrete to establish" should read --the concrete, to establish--.

Column 2, line 17, "the stress existing" should read --the existing stress--.

Column 2, line 18, "the concrete built" should read --the concrete, built--.

UNITED STATES PATENT AND TRADEMARK OFFICE
CERTIFICATE OF CORRECTION

PATENT NO. : 6,029,526
DATED : Feb. 29, 2000
INVENTOR(S) : Alex I Feldman, et al.

It is certified that error appears in the above-identified patent and that said Letters Patent is hereby corrected as shown below:

Column 2, line 29, "output reading in the strain gauge" should read --output from the strain gauge--.

Column 2, line 32, "segment but far" should read --segment, but far--.

Column 2, line 48, "flat jacks which" should read --flat jacks, which--.

Column 2, line 49, "pressure to side walls" should read --pressure to the side walls--.

Column 3, line 3, "the externally applied load." should read -- the applied external load.--.

Column 3, line 19, "the drawings a typical" should read --the drawings, a typical--.

Column 3, lines 26-27, "binder as is well" should read --binder, as is well--.

Column 3, lines 27-28, "very old perhaps" should read --very old, perhaps--.

Column 3, line 28, "early 1900's or" should read --early 1900's, or--.

Column 3, line 40, "concrete as by" should read --concrete, as by--.

Column 3, line 44, "cut as the" should read --cut, as the--.

Column 3, line 49, "one example for" should read --one example, for--.

UNITED STATES PATENT AND TRADEMARK OFFICE
CERTIFICATE OF CORRECTION

PATENT NO. : 6,029,526
DATED : Feb. 29, 2000
INVENTOR(S) : Alex I. Feldman, et al.

It is certified that error appears in the above-identified patent and that said Letters Patent is hereby corrected as shown below:

Column 3, lines 49-50, "liner the slots" should read --liner, the slots--.

Column 3, line 63, "source as is well known." should read --source, as is well known.--.

Column 3, line 67, "gauge again reads the" should read --gauge returns to the--.

Column 3, line 67, "baseline readout" should read --baseline reading--.

Column 4, line 4, "flat jacks the original" should read --flat jacks, the original--.

Column 4, line 20, "segment but far" should read --segment, but far--.

Column 4, lines 20-21, "one h, about" should read --one h (about--.

Column 4, line 62, "six-eight" should read --six and eight--.

Column 5, line 1, "inches+½" should read --inches + ½--.

Column 5, line 1, "inch+½" should read --inch + ½--.

Column 5, lines 2-3, "segment the depth" should read --segment, the depth--.

Column 5, lines 5-6, "width w is of normal" should read --width w is equal to the normal--.

Column 5, line 19, "edges and, of course, are relatively" should read --edges and are relatively--.

UNITED STATES PATENT AND TRADEMARK OFFICE
CERTIFICATE OF CORRECTION

PATENT NO. : 6,026,529
DATED : Feb. 29, 2000
INVENTOR(S) : Alex I. Feldman, et al.

It is certified that error appears in the above-identified patent and that said Letters Patent is hereby corrected as shown below:

Column 5, line 20, "Preferably again the pressure" should read --Preferably again, the pressure--.

Column 5, line 36, "From the foregoing it will" should read --From the foregoing, it will--.

Claim 8, column 6, line 28, "segment is equals" should read --segment equals--.

Claim 13, column 7, line 23-24, "slots being providing about" should read --slots providing about--.

Signed and Sealed this

Second Day of January, 2001

Attest:

Attesting Officer

Q. TODD DICKINSON
Commissioner of Patents and Trademarks